United States Patent [19]

Overton, Jr. et al.

[11] Patent Number: 5,008,622
[45] Date of Patent: Apr. 16, 1991

[54] SUPERCONDUCTIVE IMAGING SURFACE MAGNETOMETER

[75] Inventors: William C. Overton, Jr., Los Alamos; David B. van Hulsteyn, Santa Fe; Edward R. Flynn, Los Alamos, all of N. Mex.

[73] Assignee: United States Department of Energy, Washington, D.C.

[21] Appl. No.: 454,607

[22] Filed: Dec. 21, 1989

[51] Int. Cl.$^5$ .................. G01R 33/02; G01R 33/035
[52] U.S. Cl. .................................... 324/248; 505/846
[58] Field of Search .................. 324/248, 262; 505/846

[56] References Cited

U.S. PATENT DOCUMENTS 3,435,337  3/1969  Inouye et al. ..................... 324/248
3,924,176  12/1975 Fletcher et al. ................... 324/248
4,700,135  10/1987 Hoenig ............................. 324/248

OTHER PUBLICATIONS

I. W. C. Overton, Jr., D. B. van Hulsteyn, and E. R. Flynn, "Use of Superconducting Imaging Surfaces to Enhance Detection of Weak Magnetic Sources by SQUID Systems", Los Alamos National Laboratory document LA-11473-MS, (issued Jan. 1989).

W. C. Overton, Jr., D. B. van Hulsteyn, and E. R. Flynn, "Use of Superconducting Plates and Shells to Deflect Magnetic Noise Fields", Application to MEG, Proc. of the Annual Conf. of the IEEE Engineering in Medicine and Biology Soc., vol. II, p. 1293 (1989).

*Primary Examiner*—Walter E. Snow
*Attorney, Agent, or Firm*—Milton D. Wyrick; Paul D. Gaetjens; William R. Moser

[57] ABSTRACT

An improved pick-up coil system for use with Superconducting Quantum Interference Device gradiometers and magnetometers involving the use of superconducting plates near conventional pick-up coil arrangements to provide imaging of nearby dipole sources and to deflect environmental magnetic noise away from the pick-up coils. This allows the practice of gradiometry and magnetometry in magnetically unshielded environments. One embodiment uses a hemispherically shaped superconducting plate with interior pick-up coils, allowing brain wave measurements to be made on human patients. another embodiment using flat superconducting plates could be used in non-destructive evaluation of materials.

44 Claims, 5 Drawing Sheets

SUPERCONDUCTIVE IMAGING SURFACE MAGNETOMETER

BACKGROUND OF THE INVENTION

The present invention generally relates to the use of Superconducting Quantum Interference Devices (SQUIDs) and, more specifically, to sensors for use with SQUIDs in magnetometry and gradiometry.

Superconducting Quantum Interference Devices (SQUIDs) are widely used to detect and quantify extremely weak magnetic signals, such as those emanating from the brain of a human or an animal. In magnetoencephalography, brain wave signals ranging from 10 to $10^3$ femto Teslas (fT) are measured. Other uses include near magnetic field antennas, high sensitivity magnetometers, and non-destructive material evaluators.

Because of their great sensitivity, SQUID magnetometers are subject to having the signal of interest swamped by large noise backgrounds. Contributors to these noise backgrounds include the earth's magnetic field, and cultural noise such electrical power lines and cords, and automobiles. For example, the natural pulsations of the earth's magnetic field produce noise with a magnitude typically ranging from $10^5$ to $10^8$ fT. Noise fields of this magnitude tend to overwhelm the small signals of interest, making even the most sophisticated digital data processing techniques extremely difficult.

The use of superconducting sensor coil systems in conjunction with SQUID detectors is well known. These sensor coils typically have inductances of 1 or 2 microhenries in order to match the inputs of rf or dc SQUIDs. Typically, SQUID systems are arranged in either the magnetometer mode (single oriented sensor coil), the first-order gradiometer mode (two coils in either axial or planar arrangement), or the second-order gradiometer mode (two first-order gradiometers connected in series opposition).

The conventional attempt at solving the swamping problem is the use of superconducting gradiometry mode. With gradiometry, as stated above, sensor coils for the SQUID involve a pair of superconducting coils connected in series opposition in an attempt to electrically cancel the input of extraneous magnetic noise. However, unavoidable structural imperfections can limit the degree of cancellation obtainable.

When these gradiometers are used inside expensive magnetically shielded rooms, significant signal to noise ratio improvement can be realized. Even with this expensive configuration, however, noise in the 0.1 to 100 Hz range can sometimes interfere with SQUID magnetometer measurements.

An important point concerning the interfering magnetic noise is that its sources are distant with respect to the magnetic signals of interest. This means that the magnetic noise lines are substantially parallel as they approach the SQUID magnetometer.

The present invention provides apparatus for greatly improving and simplifying SQUID magnetometry detection through the use of superconducting surfaces used in conjunction with magnetometry and gradiometry coils. This configuration significantly reduces noise pick up while allowing SQUID measurements to be conducted in unshielded rooms, such as a hospital rooms and doctors' offices.

It is therefore an object of the present invention to provide apparatus for inhibiting noise pick up by SQUID magnetometers and gradiometers.

It is a further object of the present invention to provide SQUID magnetometry and gradiometry sensor apparatus that will operate successfully in an area which is not magnetically shielded.

It is a further object of the present invention to provide SQUID magnetometry and gradiometry sensor apparatus that will measure brain electrical activity over the entire skull area of a patient.

It is a still further object of the present invention to provide SQUID magnetometry and gradiometry sensor apparatus for detecting defects in materials.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention may comprise one or more first superconducting coil means connected in series opposition to one or more second superconducting coil means for sensing nearby magnetic signals and electrically cancelling distant magnetic noise with superconducting plate means interposed between and in close proximity to the one or more first and second superconducting coil means for imaging the nearby magnetic signals and deflecting the distant magnetic noise away from the first and second superconducting coil means. The one or more first and second superconducting coil means are connected to a SQUID.

In a further aspect of the present invention and in accordance with its principles and purposes, apparatus for detecting nearby magnetic sources by performing imaging SQUID magnetometry and gradiometry comprise superconducting plate means for imaging said nearby magnetic sources and deflecting distant magnetic field lines; first and second superconducting coil means located on one side of and in near proximity to the superconducting plate means, the first and second superconducting coil means being connected together in series opposition for detection of nearby magnetic signals and cancellation of noise from distant magnetic sources; wherein the first and second superconducting coils are connected to individual SQUIDs.

In a further aspect of the invention, and in accordance with its objects and purposes, the invention may comprise one or more first superconducting coil means connected in series opposition to one or more second superconducting coil means for sensing nearby magnetic signals and electrically cancelling noise; and superconducting plate means interposed between and in close proximity to the first and second superconducting coils for deflecting magnetic lines of the noise away from the first and second superconducting coils. The coils are connected to a SQUID.

In another aspect of the invention, and in accordance with its objects and purposes, the invention may comprise superconducting plate means for diverting distant magnetic field lines, with first and second superconducting coils located on one side of and in near proximity to said superconducting plate means. The superconducting coils are connected together in series opposition to detect nearby magnetic signals and to cancel noise from distant magnetic sources, and are further connected to individual SQUIDs.

In yet another aspect of the invention, and in accordance with its objects and purposes, the invention may comprise first and second superconducting coil means for detecting nearby magnetic signals for output to an associated SQUID, and for cancelling noise from distant magnetic sources connected together in series opposition and having the axes of said first and second superconducting coil means parallel to the principal axis of a superconducting plate means. The superconducting plate means is interposed between said first and second superconducting coil means for diverting field lines of distant magnetic sources away from said first and second superconducting coil means. A superconducting plate in the shape of a hemisphere having interior and exterior surfaces, and a plurality of superconducting coils spaced apart in near proximity to the interior surface of the hemisphere, wherein each of the superconducting coils is connected to an individual SQUID.

In a still further aspect of the present invention and in accordance with its principles and purposes, a method of sensing nearby magnetic signals utilizing imaging SQUID magnetometry and gradiometry comprises the steps of placing one or more superconducting coils connected as a magnetometer or gradiometer near the nearby magnetic signal of interest, deflecting noise from distant magnetic sources away from the one or more superconducting coils using a superconducting plate placed adjacent to the one or more superconducting coils; detecting the nearby magnetic signal of interest and an image of the nearby magnetic signal of interest induced on the superconducting plate; and outputting the magnetic signal of interest and the image of the nearby magnetic signal of interest to one or more SQUIDs.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

The present invention allows the sensing of nearby small magnetic signals by SQUID detectors in a magnetically unshielded environment. Of course, as with all previous magnetometers and gradiometers, conventional RF shielding is necessary. This is conventionally done with a thin beryllium-copper sheet encasing the magnetometer or gradiometer.

Effective sensing of small magnetic signals is often not possible with conventional SQUID sensing coils because of the swamping of the signals of interest by ambient magnetic noise. This improvement in SQUID magnetometry and gradiometry detection is enabled by the use of superconducting plates in conjunction with more conventional sensor coils. This allows deflection of magnetic noise away from the sensor coils, and makes use of the well known image effect for magnetic signals. The effects of the present invention can be best appreciated by reference to FIG. 1.

Figure 1:
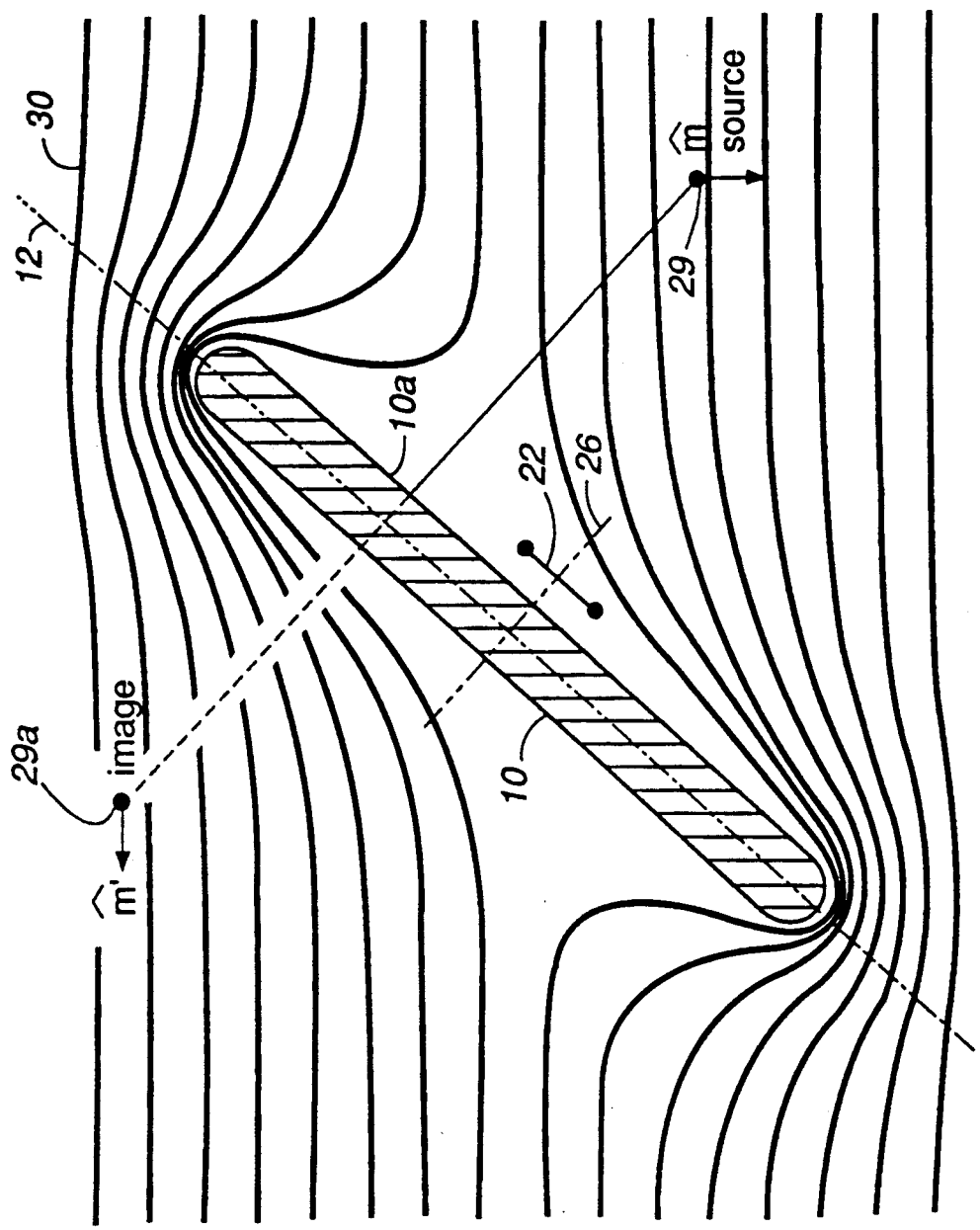
FIG. 1 is a cross-sectional view of one embodiment of the present information involving a flat superconducting plate tilted at an angle of 45° with respect to external magnetic noise field lines, with a single superconducting sensor coil located nearby. Also shown is a dipole source m and its image m'.

In FIG. 1, generally flat superconducting plate 10 is shown positioned at an angle of 45° with reference to field lines 30, which schematically represent ambient magnetic noise from distant sources. Because of the assumed distance between these magnetic noise sources and plate 10, lines 30 are substantially parallel as they approach plate 10. Superconducting plate 10 can be made of any superconducting material, having either a high or low transition temperature. Lead has proved to be a suitable material for use with liquid helium.

Superconducting sensor coil 22 is shown in close proximity to plate 10 with its axis 26 perpendicular to axis 12 through the center line of plate 10. Coil 22 is constructed of fine superconducting wire to have an inductance of approximately 1.5 to 1.8 microhenries to match the typical SQUID input inductance of approximately 2 microhenries. Twisted and shielded leads 22a connect coil 22 to its associated SQUID (not shown), which would be located an appropriate distance above plate 10. Coil 22 can also be constructed of any suitable high or low temperature superconducting material.

Nearby magnetic source 29, which could be a brain dipole, is located a short distance (in relation to the magnetic noise sources producing lines 30) from plate 10, and produces an average magnetic field over the area of coil 22. Because plate 10 is a superconductor and has, in effect, infinite electrical conductivity, source 29 will induce a current on surface 10a of plate 10 which can be visualized as image dipole 29a located the same distance from surface 10a as source 29. The effect of image dipole 29a is to also produce an average field over the area of coil 22. These average fields cause superconducting coil 22 to develop a current in order to maintain constant the magnetic flux it surrounds. This current is the signal current conveyed to the SQUID to recognize the presence of dipole 29. When measured by the SQUID electronics, the current is proportional to the difference between the average field produced by dipole 29 and the average field produced by its image dipole 29a. This effect is well demonstrated by placing a magnet above a piece of superconducting material and observing that it is suspended above the material by its repulsion of the magnet's field.

One of the indications of a superconducting (the Meisener effect) material is its repulsion of a magnetic field. This means that a magnetic field must go to zero inside a superconductor. It is because of this effect that noise lines 30 are shown as being deflected around plate 10.

It is to be appreciated that, absent plate 10, noise field lines 30 would pass directly through coil 22. However, with plate 10 at any angle with respect to noise lines 30, with the possible exception of 0°, some distortion of lines 30 away from coils 22, 24 is accomplished. This deflection is at a maximum when plate 10 is perpendicular to lines 30, and decreases as the angle between plate 10 and lines 30 approaches 0°.

A single magnetometer coil 22 located as shown in front of a superconducting plate, as shown in FIG. 1, because of the image principle, behaves like a conventional first-order two coil magnetic gradiometer for detecting nearby dipole sources. The conventional first-order gradiometer reduces magnetic noise by having its two coaxial coils connected in series opposition, a technique that in theory should provide complete noise cancellation. However, the actual degree of cancellation depends on the mechanical perfection of the entire gradiometer, perfection which is in practice almost impossible to achieve.

Although cancellation of magnetic noise by the single coil image magnetometer described in FIG. 1 also depends on mechanical perfection, the noise field strength in the vicinity of coil 22 is greatly reduced by the noise deflection properties of superconducting plate 10. Additionally, imaging also provides for sensing of the current induced on surface 10a by magnetic source 29. Because of this, the image magnetometer according to the present invention exhibits a significant advantage over the conventional first-order gradiometer.

Figure 2:
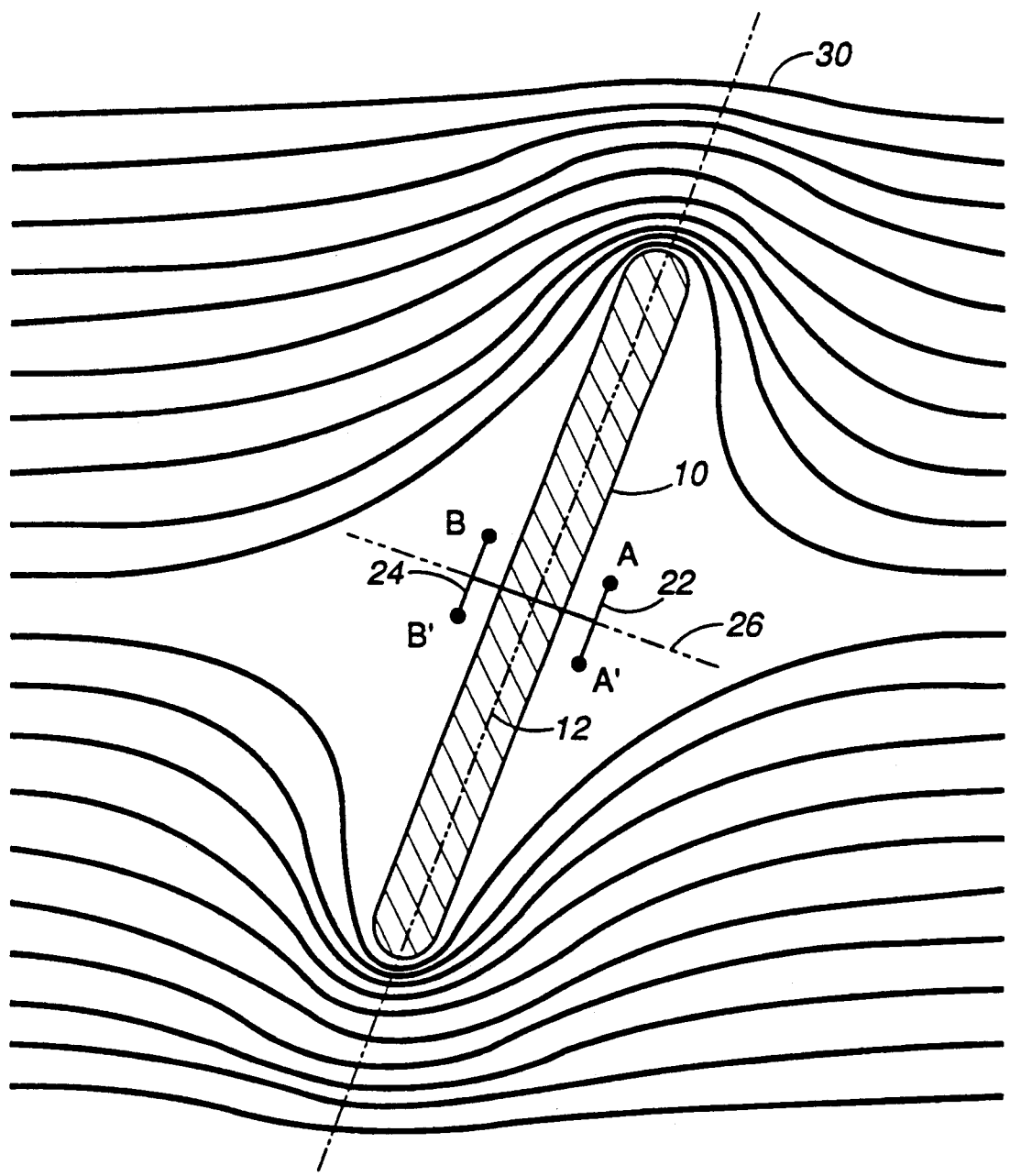
FIG. 2 is a cross-sectional view of another embodiment of the present invention wherein a flat superconducting plate is tilted at an angle of 22.5° with respect to the external field lines, and has superconducting coils on each side, with their axes perpendicular to the principal axis of the plate.

Another embodiment of the present invention is illustrated in FIG. 2. Here, superconducting coil 22 and superconducting coil 24 are positioned on each side of generally flat superconducting plate 10, which is shown positioned at an angle of 22.5° with reference to ambient magnetic noise lines 30. Again, magnetic noise lines 30 are assumed to be parallel as they approach superconducting plate 10.

Superconducting sensor coils 22, 24 are shown in close proximity to plate 10 with their axes 26 perpendicular to axis 12 through the center line of plate 10. Coil 22 is connected to coil 24 in series opposition, as is typical of a first-order gradiometer. Although conventional second-order gradiometers are certainly an improvement over prior sensor coil systems, they are not totally effective in cancelling all distant magnetic noise as was previously discussed, even in a magnetically shielded environment, due to unavoidable mechanical variations when implemented. The present invention provides a greater improvement through source imaging and deflection of noise fields such as noise field 30 away from superconducting coils 22, 24.

As illustrated in FIG. 2, magnetic noise field lines 30 cause a noise field at point A on coil 22 equal to the field at point B' on coil 24. Likewise, the noise field at point A' on coil 22 is equal to the field at point B on coil 24. This allows noise cancellation to be accomplished by connecting coil 22 to coil 24 in series opposition. Of course, the desired signal from nearby dipole source 29 will produce signals only in coil 22. Tests on apparatus without RF shielding and using a Hemholtz coil to produce a 100 Hz field equivalent to environmental magnetic noise have yielded noise rejection from 330,000 parts to one part.

The extent of deflection of magnetic noise lines 30 by superconducting plate 10, as a function of the angle between plate 10 and field lines 30, is easily seen by comparing FIG. 1 with FIG. 2. In FIG. 1, with plate 10 at an angle of 45° with respect to field lines 30, the distance from point A' on coil 22 to the nearest field line 30 is much smaller than the distance between point A' on coil 22 and the nearest field line 30 in FIG. 2, where the angle of plate 10 is 22.5°.

Figure 3:
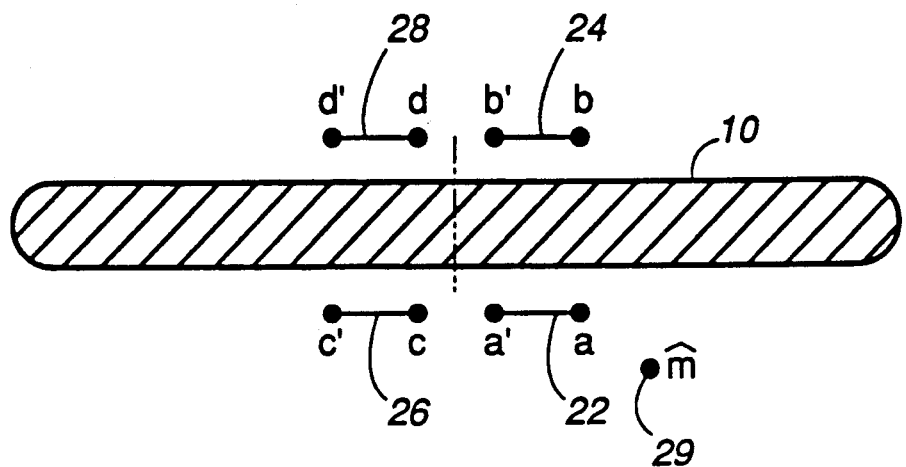
FIG. 3 is a cross-sectional view of another embodiment of the present invention in which a pair of sensor coils is located on each side of the superconducting plate, with their axes perpendicular to principal axis of the plate.

Another embodiment of the present invention is shown in FIG. 3. Here, pair of coils 22, 26 is located on one side of superconducting plate 10, and pair of coils 24, 28 is located on the opposite side. Again, the axes of coils 22, 26 and 28 are perpendicular to plate 10. As in FIG. 2, field lines will have a magnitude at Point a on coil 22 equal to the magnitude at Point d' on coil 28. Likewise, the magnitude at Point c on coil 26 equals the magnitude at Point b' on coil 24. Because of this, noise cancellation will be accomplished by connecting coil 22 in series opposition to coil 28, and by connecting coil 26 in series opposition to coil 24. Any magnetic signal produced by nearby dipole source 29 will produce signals in only coil 22 and coil 26.

Figure 4:
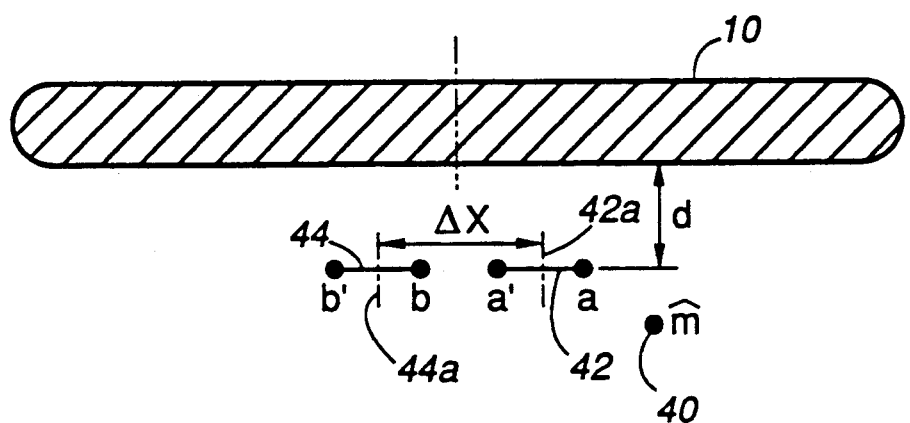
FIG. 4 is a cross-sectional view of yet another embodiment of the present invention in which a pair of sensor coils is located on one side of a superconducting plate, with their axes perpendicular to the principal axis of the plate.

In yet another embodiment, shown in FIG. 4, a conventional planar gradiometer is disposed near the midpoint of superconducting plate 10. Coils 42, 44 are identical, and have their axes 42a and 44a separated by a distance $\Delta x$ and perpendicular to plate 10. In a conventional planar gradiometer, this arrangement measures the cross derivative $\Delta B_z/\Delta x$. However, because of imaging, each coil 42, 44 will also produce a signal like an axial gradiometer of the form $\Delta B_z/\Delta z$. The net result is:

$$(\Delta B_z/\Delta z\{\text{at coil 42}\} - \Delta B_z/\Delta z\{\text{at coil 44}\})/\Delta x. \quad (1)$$

This embodiment is extremely effective in cancelling noise while recognizing the fields from nearby dipole source 40.

Figure 5:
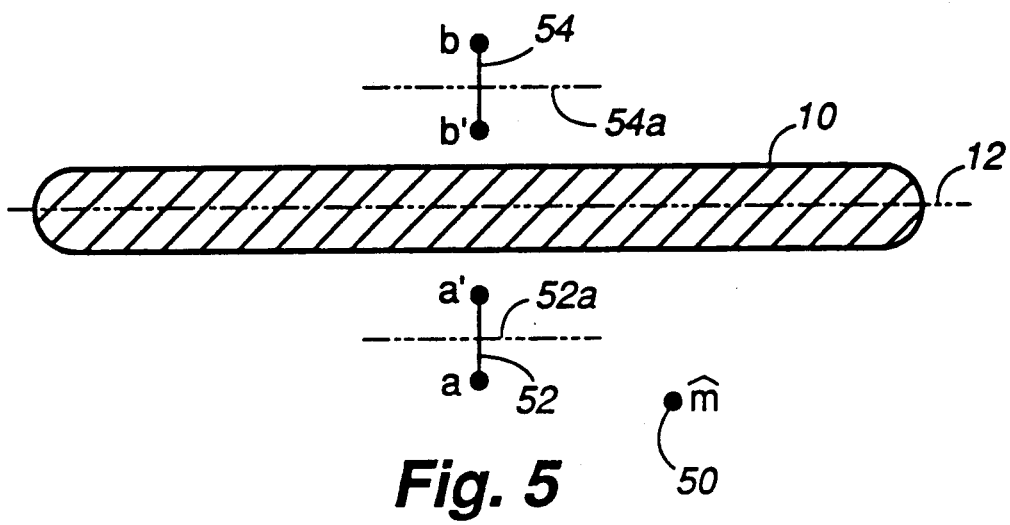
FIG. 5 is a cross-sectional view of yet another embodiment of the present invention in which a sensor coil is located on each side of a superconducting plate, with the axes of the coils parallel to the principal axis of the plate.

A still further embodiment of the present invention is illustrated in cross-section in FIG. 5. Here, coil 52 and coil 54 are again on opposite sides of superconducting plate 10, but their axes 52a and 54a are parallel to axis 12 of plate 10. The two coils 52, 54 are again connected in series opposition. In this configuration, the tangential component of the field from nearby dipole source 50 will produce a signal in tangentially oriented coil 52. Tangentially oriented coil 54 will serve to further cancel noise from distant sources.

In all of the foregoing embodiments, the coils may be deposited on sapphire substrates which are in thermal contact with plate 10. Any suitable method of cooling plate 10 below its transition temperature could be employed. Possible methods include, but are not limited to, placing tubing carrying a coolant in thermal contact with plate 10, or immersing plate 10 in a bath of coolant.

Figure 6:
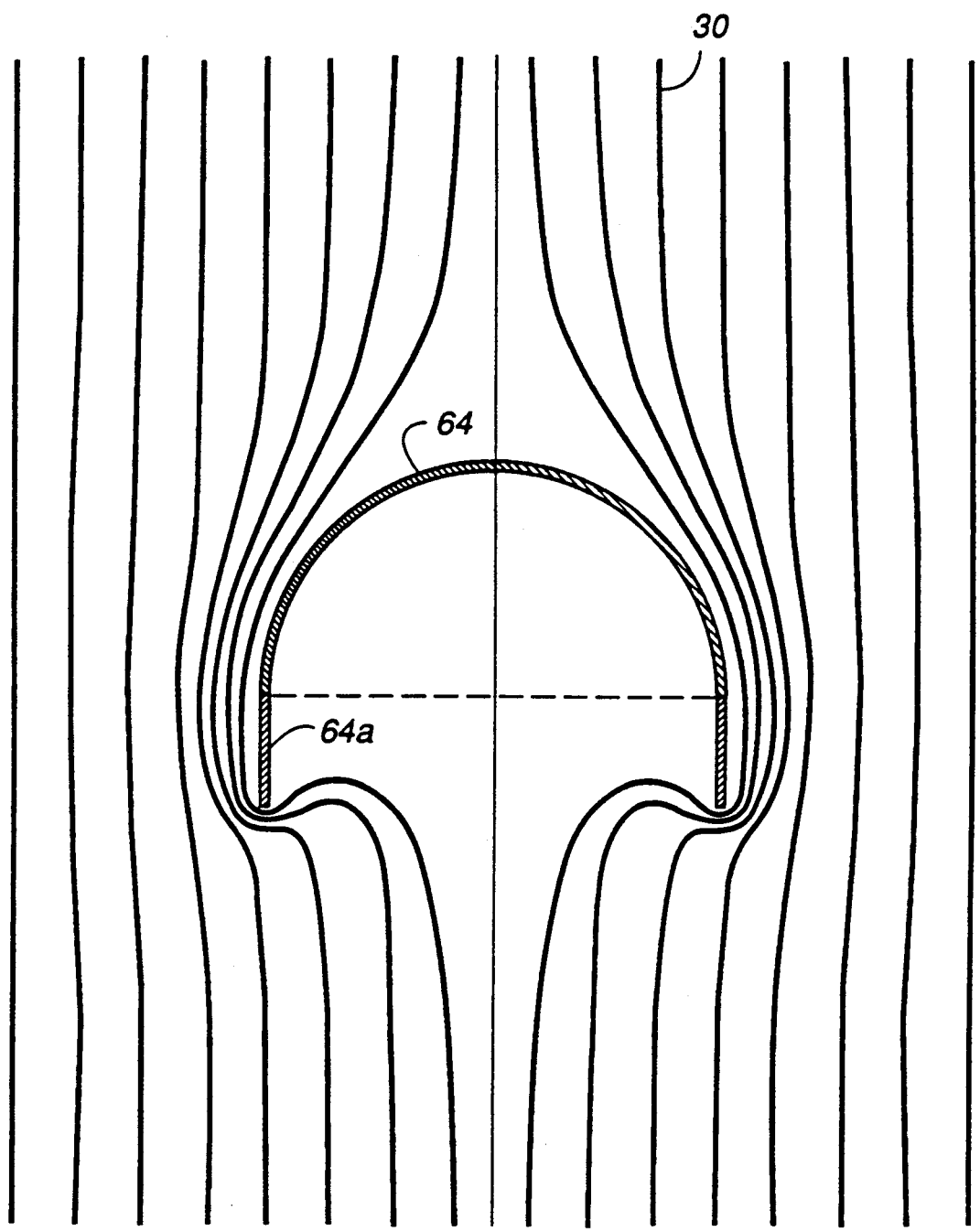
FIG. 6 is a cross-sectional view of a hemispherically shaped superconducting plate along with magnetic noise field lines from distant sources.

Referring now to FIG. 6, there can be seen hemispherically shaped plate 64 immersed in magnetic noise field lines 30. Attached to hemispherically shaped plate 64 is cylindrical extension 64a, whose function is to provide sufficient material to cover a human head. Hemispherically shaped plate 64 and cylindrical extension 64a are, as with the previous embodiments, constructed of superconducting materials.

As illustrated in FIG. 6, magnetic noise field lines 30 are deflected around hemispherically shaped plate 64 and cylindrical extension 64a, due to their being constructed of a superconducting material. Noise field lines 30 do not enter the interior portions of hemispherically shaped plate 64 and cylindrical extension 64a far enough to interfere with measurements. It should be noted that this orientation of field lines 30 is a worst case. Noise originating from other directions would cause even less encroachment.

Figure 7:
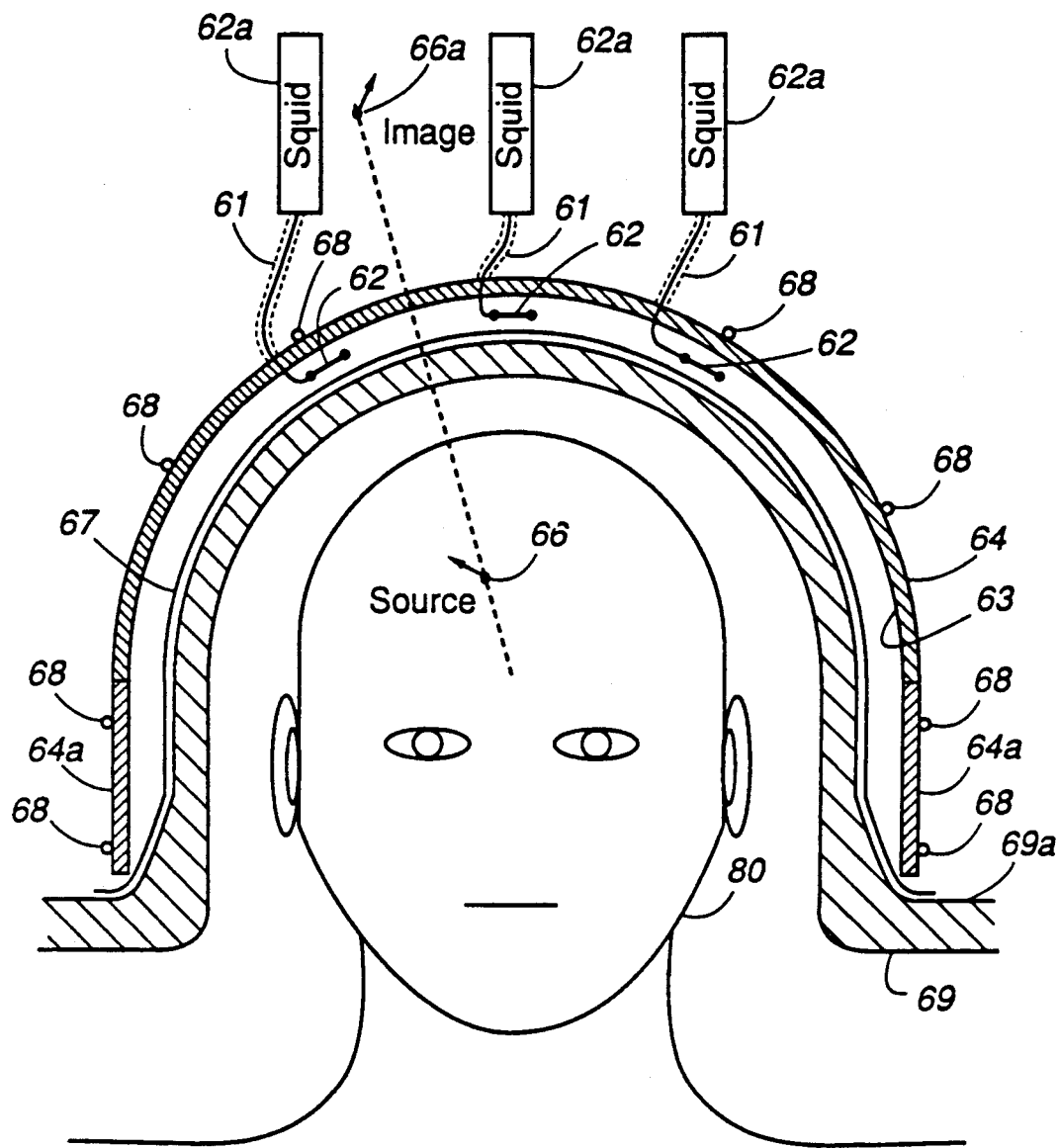
FIG. 7 is a cross sectional view of an embodiment of the present invention wherein the hemispherical superconducting plate is shown in place over a patient, with superconducting coils disposed about its interior surface. The bottom of the enclosing dewar is shown as well as tubing to carry the coolant.

An embodiment, utilizing hemispherically shaped plate 64 with cylindrical extension 64a, and which may be medically important, is shown in cross-section and in place over head 80 in FIG. 7. Here a plurality of coils, generically referred to as superconducting magnetometer pick-up coils 62, are disposed nearby and generally over the interior surface 63 of hemispherical superconducting plate 64, although for clarity only three coils 62 are illustrated. No coils are located outside plate 64, as there is no need for noise cancellation with this embodiment.

As previously discussed and illustrated in FIG. 6, noise field lines are deflected harmlessly around the outside of plate 64 and cylindrical extension 64a, because they are constructed of a superconducting material. Coils 62 can be distributed across interior surface 63 in positions calculated to detect minute magnetic signals emitted from locations within the brain, such as from source dipole 66 and its image 66a, located outside shell 64 to represent surface currents on interior surface 63. With source dipole 66 located anywhere within head 80 other than at the center of hemispherically shaped plate 64, image 66a is located a distance $b^2/a$ from the center of plate 64. Here, b is the radius of interior surface 63 and a is the distance from the center of plate 64 to source dipole 66.

It is important to note that for this embodiment to operate successfully, both coils 62, and source dipole 66 must be located well inside shell 64. Also, somewhat obviously, hemispherical dewar bottom 69 must accommodate hemispherical shell 64 to maintain the low temperatures required and withstand atmospheric pressure. A configuration such as this is invaluable in the exploration of the human brain. It is easy to understand that this embodiment could be used in hospital rooms and doctors' offices without the requirement for magnetic shielding of the room.

As shown in FIG. 7, shell 64 has one or more superconducting cylindrical extensions 64a attached so that head 80 is completely covered. Extensions 64a end just above dewar bottom 69. For heat shielding, a layer of insulating material 67, such as SUPERINSULATION ® available from Metallized Products, Inc., 37 East Street, Winchester, Mass. 01890 overlies interior surface 69a of dewar bottom 69. SUPERINSULATION ®is a Mylar ® film onto which onto which a layer of aluminum, approximately 0.001 in, thick, has been deposited. RF shielding could be accomplished by placing a thin (approximately 0.002-0.005 in.) beryllium-copper sheet (not shown) between insulating material 67 and pick-up coils 62. A vacuum is maintained in the space created by shell 64 and interior surface 69a for maintaining low temperatures by vacuum isolation.

Tubes 68 encircle and are in thermal contact with hemispherical superconducting shell 64. Tubes 68 carry liquid helium, liquid nitrogen, or other coolant, depending on whether the material comprising hemispherical superconducting shell 64 is a conventional or high $T_c$ superconductor, to cool shell 64 to a temperature below its transition temperature. Cooling could also be immersing the entire shell 64 in the coolant, or by creating an additional space (not shown) in the area between shell 64 and interior surface 69a, which space could be flooded with the coolant.

Coils 62 may be deposited on sapphire substrates which would be in direct contact with surface 63. Because sapphire of high purity has good thermal conductivity at low temperatures (near 4K), it will help maintain coils 62 below the transition temperature of the material from which they are constructed.

As shown, each superconducting coil 62 is connected to its associated SQUID 62a through twisted shielded cable 61. According to the application, there may be on the order of 25 or more pairs of coils 62 and SQUIDs 62a. This is to insure complete coverage of all desired areas of the brain. As with other embodiments, the signal pick-up is enhanced by use of the imaging technique, where coils 62 detect the signal from source 66, as well as from its image 66a, representing surface currents on surface 63.

In all of these embodiments, for low temperature superconductor materials, the superconducting coils can be approximately 7 turns of niobium or niobium titanium superconducting wire. The twisted shielded cable can be made of wires also made of niobium with TEFLON ® insulation. A twisted pair of these niobium wires are inserted into a lead shield sheath. However, coils and wires of a differing number of turns or of different superconducting materials could also be used depending on whether low or high temperature superconducting materials are used. The same is true for superconducting plates 10, and shell 62. For example lead could be utilized. However, other materials could also be used. Of course, with different materials, consideration must be given to each material's transition temperature in order to determine the appropriate cooling medium.

Niobium has a transition temperature of approximately 10K, and lead has a transition temperature of approximately 7.2K. With liquid helium being circulated in tubes 68 at a temperature at sea level of 4.2K, both materials would be maintained well below their transition temperatures. However, nothing herein should be construed as limiting the invention to the particular compositions of coils and wire described herein. The only requirement is that the transition temperature, $T_c$, be high enough above the temperature of the cooling media to maintain the material in its superconducting state.

Persons having skill in this art will appreciate that the present invention, in addition to having application to measurement of physiological sources, can also find application to the detection of defects in materials. This is extremely important in many manufacturing processes.

The foregoing description of the preferred embodiments of the invention have been presented for purposes of illustration and description. It is not intended to be exhaustive or to limit the invention to the precise form disclosed, and obviously many modifications and variations are possible in light of the above teachings. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for detecting nearby magnetic sources by performing imaging SQUID magnetometry and gradiometry comprising:
   one or more first superconducting coil means connected in series opposition to one or more second superconducting coil means for sensing nearby magnetic signals and electrically cancelling distant magnetic noise;
   superconducting plate means interposed between and in close proximity to said one or more first and second superconducting coil means for imaging said nearby magnetic signals and deflecting said distant magnetic noise away from said first and second superconducting coil means;
   wherein said one or more first and second superconducting coil means are connected to a SQUID.

2. The magnetometry and gradiometry apparatus as described in claim wherein said one or more first and second superconducting coil means and said superconducting plate means are maintained at a temperature sufficiently low to cause said one or more first and second superconducting coil means and said superconducting plate means to be superconducting.

3. The apparatus as described in claim 2, in which said cooling means comprises tubing in thermal contact with said superconducting plate, said tubing containing a coolant.

4. The apparatus as described in claim 2, in which said cooling means comprises a bath of coolant into which said one or more first and second superconducting coil means and said superconducting plate means are immersed.

5. The magnetometry and gradiometry apparatus as described in claim wherein said one or more first and second superconducting coil means comprise niobium wires.

6. The magnetometry and gradiometry apparatus as described in claim 1, wherein said one or more first and second superconducting coil means comprise niobium-titanium wires.

7. The magnetometry and gradiometry apparatus as described in claim 1 wherein said one or more first and second superconducting coil means are each deposited on a sapphire substrate, said sapphire substrates being in thermal contact with said superconducting plate means.

8. The magnetometry and gradiometry apparatus as described in claim 1, wherein said superconducting plate means comprises lead.

9. Apparatus for detecting nearby magnetic sources by performing imaging SQUID magnetometry and gradiometry comprising:
   superconducting plate means for imaging said nearby magnetic sources and deflecting distant magnetic field lines;
   first and second superconducting coil means located on one side of and in near proximity to said superconducting plate means, said first and second superconducting coil means being connected together in series opposition for detection of nearby magnetic signals and cancellation of noise from distant magnetic sources;
   wherein said first and second superconducting coils are connected to individual SQUIDs.

10. The apparatus as described in claim 9, further comprising cooling means for maintaining said superconducting plate means and said first and second superconducting coil means maintained at a temperature sufficiently low to cause said first and second superconducting coil means and said superconducting plate to be superconducting.

11. The apparatus as described in claim 9, in which said cooling means comprises tubing in thermal contact with said superconducting plate, said tubing containing a coolant.

12. The apparatus as described in claim 9, in which said cooling means comprises a bath of coolant into which said first and second superconducting coil means and said superconducting plate means are immersed.

13. The magnetometry and gradiometry apparatus as described in claim 9, wherein said first and second superconducting coil means comprise niobium wires.

14. The magnetometry and gradiometry apparatus as described in claim 9, wherein said first and second superconducting coil means comprise niobium-titanium wires.

15. The magnetometry and gradiometry apparatus as described in claim 9 wherein said first and second superconducting coil means are deposited on sapphire substrates which are in thermal contact with said superconducting plate means.

16. The magnetometry and gradiometry apparatus as described in claim 9, wherein said superconducting plate means comprises lead.

17. Apparatus for detecting nearby magnetic sources by performing imaging SQUID magnetometry and gradiometry comprising:
   superconducting plate means having first and second sides for imaging said nearby magnetic sources and deflecting field lines of distant magnetic sources around said superconducting plate means;
   first superconducting coil means located in close proximity to said first side of said superconducting plate means for detecting nearby magnetic signals and outputting said signals to an associated SQUID;
   second superconducting coil means located in close proximity to said second side of said superconducting plate means and connected to said first superconducting coil in series opposition for cancelling noise from distant magnetic sources;
   wherein the axes of said first and second superconducting coil means are parallel to said first and second sides of said superconducting plate means.

18. The magnetometry and gradiometry apparatus as described in claim 17, wherein said first and second superconducting coil means and said superconducting plate means are maintained at a temperature sufficiently low to cause said first and second superconducting coil means and said superconducting plate means to be superconducting.

19. The apparatus as described in claim 17, in which said cooling means comprises tubing in thermal contact with said superconducting plate, said tubing containing a coolant.

20. The apparatus as described in claim 17, in which said cooling means comprises a bath of coolant into which said first and second superconducting coil means and said superconducting plate means are immersed.

21. The magnetometry and gradiometry apparatus as described in claim 17, wherein said first and second superconducting coil means comprise niobium wires.

22. The magnetometry and gradiometry apparatus as described in claim 17, wherein said first and second superconducting coil means comprise niobium-titanium wires.

23. The magnetometry and gradiometry apparatus as described in claim 17 wherein said first and second superconducting coil means are each deposited on a sapphire substrate, said sapphire substrates being in thermal contact with said superconducting plate means.

24. The magnetometry and gradiometry apparatus as described in claim 17, wherein said superconducting plate means comprises lead.

25. Apparatus for detecting nearby magnetic sources by performing imaging SQUID magnetometry and gradiometry comprising:
   superconducting coil means connected to a SQUID for sensing nearby magnetic signals;
   superconducting plate means located in close proximity to said superconducting coil means for imaging said nearby magnetic signals and deflecting said distant magnetic noise away from said superconducting coil means;

26. The magnetometry and gradiometry apparatus as described in claim 25, wherein said superconducting coil means and said superconducting plate means are maintained at a temperature sufficiently low to cause said superconducting coil means and said superconducting plate means to be superconducting.

27. The apparatus as described in claim 26, in which said cooling means comprises tubing in thermal contact with said superconducting plate, said tubing containing a coolant.

28. The apparatus as described in claim 26, in which said cooling means comprises a bath of coolant into which said superconducting coil means and said superconducting plate means are immersed.

29. The magnetometry and gradiometry apparatus as described in claim 25, wherein said superconducting coil means comprises niobium wires.

30. The magnetometry and gradiometry apparatus as described in claim 25, wherein said superconducting coil means comprises niobium-titanium wires.

31. The magnetometry and gradiometry apparatus as described in claim 25 wherein said superconducting coil means is deposited on a sapphire substrate which is in thermal contact with said superconducting plate means.

32. The magnetometry and gradiometry apparatus as described in claim 25, wherein said superconducting plate means comprises lead.

33. Apparatus for detecting nearby magnetic sources by performing imaging SQUID magnetometry and gradiometry comprising:
   superconducting plate means generally in the shape of a hemisphere having interior and exterior surfaces for imaging said nearby magnetic sources and deflecting distant magnetic noise;
   a plurality of superconducting coil means spaced apart in near proximity to said interior surface of said hemisphere for detecting said nearby magnetic sources and said images of said nearby magnetic sources;
   wherein each of said superconducting coils is connected to an individual SQUID.

34. The apparatus as described in claim 33, further comprising cooling means for maintaining said superconducting plate means and said plurality of superconducting coil means at a temperature sufficiently low to cause said plurality of superconducting coil means and said superconducting plate to be superconducting.

35. The apparatus as described in claim 34, in which said cooling means comprises tubing in thermal contact with said superconducting plate, said tubing containing a coolant.

36. The apparatus as described in claim 34, in which said cooling means comprises a bath of coolant into which said plurality of superconducting coil means and said superconducting plate means are immersed.

37. The apparatus as described in claim 35, in which said coolant comprises liquid helium.

38. The apparatus as described in claim 35, in which said coolant comprised liquid nitrogen.

39. The magnetometry and gradiometry apparatus as described in claim 33, wherein said plurality of superconducting coil means comprise niobium wires.

40. The magnetometry and gradiometry apparatus as described in claim 33, wherein said plurality of superconducting coil means comprise niobium-titanium wires.

41. The magnetometry and gradiometry apparatus as described in claim 33 wherein each of said plurality of superconducting coil means is deposited on a sapphire substrate which is in thermal contact with said superconducting plate means.

42. The magnetometry and gradiometry apparatus as described in claim 33, wherein said superconducting plate means comprises lead.

43. The magnetometry and gradiometry apparatus as described in claim 33, further comprising one more superconducting cylindrical extensions attached to said superconducting plate.

44. A method of sensing nearby magnetic signals utilizing imaging SQUID magnetometry and gradiometry comprising the steps of:
   placing one or more superconducting coils connected as a magnetometer or gradiometer near said nearby magnetic signal of interest;
   deflecting noise from distant magnetic sources away from said one or more superconducting coils using a superconducting plate placed adjacent to said one or more superconducting coils;
   detecting said nearby magnetic signal of interest and an image of said nearby magnetic signal of interest induced on said superconducting plate;
   outputting said magnetic signal of interest and said image of said nearby magnetic signal of interest to one or more SQUIDS.

* * * * *